US00PP13891P39

(12) United States Plant Patent
Pieters

(10) Patent No.: US PP13,891 P3
(45) Date of Patent: Jun. 17, 2003

(54) CHRYSANTHEMUM PLANT NAMED 'GEDI ONE JAM'

(75) Inventor: Dirk Pieters, Staden (BE)

(73) Assignee: Pieters Plant Production, BVBA, Oostnieuwkerke (BE)

( * ) Notice: Subject to any disclaimer, the term of this patent is extended or adjusted under 35 U.S.C. 154(b) by 0 days.

(21) Appl. No.: 09/873,748

(22) Filed: Jun. 4, 2001

(65) Prior Publication Data

US 2002/0184685 P1 Dec. 5, 2002

(51) Int. Cl.[7] ..... A01H 5/00
(52) U.S. Cl. ..... Plt./291
(58) Field of Search ..... Plt./291, 292, 287

(56) References Cited

U.S. PATENT DOCUMENTS

PP10,213 P 1/1998 Wain ..... Plt./287
PP10,419 P 5/1998 Pieters ..... Plt./287

*Primary Examiner*—Bruce R. Campell
*Assistant Examiner*—June Hwu
(74) *Attorney, Agent, or Firm*—Knobbe, Martens, Olson & Bear, LLP

(57) ABSTRACT

A new and distinct Chrysanthemum plant variety characterized by a large decorative type inflorescence, consistent flowering response to short days, blooming consistently after 49 days of short day length, free branching habit, and pink ray florets which are resistant to fading with age.

1 Drawing Sheet

LATIN NAME

*Dendranthema morifolium.*

VARIETY

'Gedi One Jam'

BACKGROUND OF THE INVENTION

Figure 1:
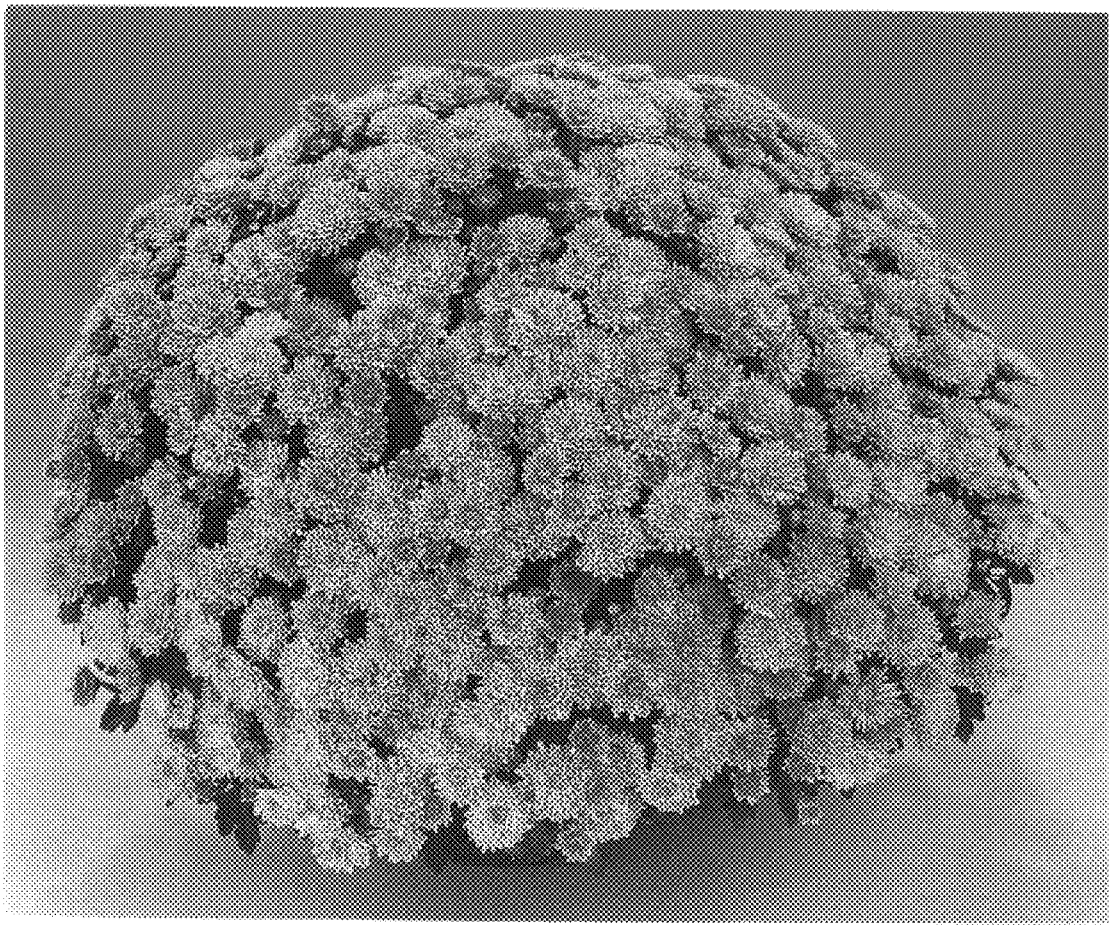

The present invention relates to a new and distinct cultivar of Chrysanthemum plant, botanically known as *Dendranthema morifolium* and herein after referred to by the cultivar mane 'Gedi One Jam.'

This new cultivar was the result of hybridization of a female parent, 'Ozenda' (U.S. Plant Pat. No. 10,419) with a male parent, 'Maribelle' (unpatented.) The new cultivar was selected in October 1997.

Asexual reproduction of the new cultivar by apical tip cutting and meristem tissue culture was performed in Oxnard, Calif. and has shown that the unique features of this new cultivar are stable and reproduced true to type on successive generations.

SUMMARY OF THE INVENTION

The cultivar 'Gedi One Jam' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'Gedi One Jam.' These characteristics in combination distinguish 'Gedi One Jam' as a new and distinct Chrysanthemum:

1. Large decorative type inflorescence;

2. Consistent flowering response to short days, blooming consistently after 49 days of short day length;

3. Free branching habit; and

4. Pink ray florets, resisting fading with age.

Plants of the new Chrysanthemum are similar to plants of the parent cultivars in most horticultural characteristics, however plants of the new cultivar differ from plants of the female parent cultivar 'Ozenda' in the following characteristics:

1. The new cultivar naturally blooms 2 weeks earlier;

2. The new cultivar has individual blooms that are more resistant to fading;

3. The new cultivar has many more ray florets than the female parent; and

4. The new cultivar has larger diameter bloom.

The new cultivar also differed from the male parent 'Maribelle' in the following characteristics:

1. The new cultivar has a different ray floret color; and

2. The new cultivar naturally blooms 2 weeks earlier.

The new cultivar can be compared to the Chrysanthemum cultivar 'Jean' (disclosed in U.S. Plant Pat. No. 10,901.) However plants of the new Chrysanthemum differed from the plants of the cultivar 'Jean' in the following characteristics:

1. New cultivar naturally blooms approximately 1 week earlier;

2. New cultivar has ray florets that are more pink than lavendar;

3. New cultivar has a more round plant shape; and

4. New cultivar has a slightly larger diameter flower.

BRIEF DESCRIPTION OF THE PHOTOGRAPHS

The photograph shows a plant of 'Gedi One Jam' grown in a 2 gallon container. One cutting was used in the pot, planted mid-May and grown under outdoor field conditions.

DETAILED BOTANICAL DESCRIPTION

In the following description, color references are made to The Royal Horticultural Society Colour Chart except where general terms of ordinary dictionary significance are used. The following observations and measurements describe plants grown in a commercial field in Oxnard, Calif. in the month of September 2000, 124 days from rooted cuttings. The growing conditions range from 60° to 65° F. at night to 70° to 85° F. during the day. Measurements and numerical values represent averages of typical flowering types.

Botanical classification: *Dendranthema morifolium* cultivar 'Gedi One Jam'.
Commercial classification: Garden-type Chrysanthemum.
Parentage: Hybridization of female parent 'Ozenda' (U.S. Plant Pat. No. 10,419) and male parent 'Maribelle' (unpatented).

PROPAGATION

Time to Rooting: 7 to 14 days at approximately 21° C.
Root description: Fine, fibrous.

PLANT

Growth habit: Mounding herbaceous perennial.
Height: Approximately 30 cm.
Growth rate: Moderate.
Plant spread: Approximately 33 cm.
Branching characteristics: Free branching.
Length of lateral branches: Approximately 25 cm.
Number of leaves per lateral branch: Approximately 28.
Stem color: Near 137A.

FOLIAGE

Leaf:
- *Arrangement.*—Alternate, single.
- *Average length.*—Approximately 8 cm.
- *Average width.*—Approximately 5.2 cm.
- *Shape of blade.*—Ovate.
- *Apex.*—Acuminate.
- *Base.*—Attenuate.
- *Attachment.*—Stalked.
- *Margin.*—Pinnately lobed and toothed.
- *Texture of top surface.*—Lightly pubescent.
- *Texture of bottom surface.*—Lightly pubescent.
- *Color.*—Young foliage upper side: Near 138A. Young foliage under side: Near 138A. Mature foliage upper side: Near 138A. Mature foliage under side: Near 138A. Venation upper side: Near 138C. Venation under side: Near 138C.

Petiole:
- *Average length.*—Approximately 3.2 cm.
- *Color.*—138A.
- *Diameter.*—2 mm.

BLOOM

Inflorescence:
- *Flowering habit.*—Induced by darkness period greater than 13.5 hours, approximately 49 days of appropriate day length required to induce and develop blooms.
- *Inflorescence form.*—Decorative.
- *Natural flowering season.*—Approximately mid-September.
- *Number of inflorescences per stem.*—Approximately 11.
- *Inflorescence diameter.*—Approximately 8.3 cm.
- *Inflorescence depth.*—2.3 cm.
- *Inflorescence longevity on plant.*—Approximately 24–29 days.
- *Persistence.*—Persistent.

Ray florets:
- *Appearance.*—Matte.
- *Texture.*—Smooth.
- *Average number per flower.*—Approximately 300.
- *Shape. Oblanceolate.*
- *Margin.*—Entire.
- *Apex.*—Obtuse.
- *Length.*—Approximately 4.2 cm.
- *Width.*—Approximately 1.1 cm.
- *Color.*—Upper surface at first opening: Near 66D. Upper surface at maturity: Near 62C. Upper surface at fading: Near 62D. Under surface at first opening: Near 59D. Under surface at maturity: Near 62B. Under surface at fading: Near 62C.

Disc florets:
- *Appearance.*—Shiny.
- *Texture.*—Smooth.
- *Average number per flower.*—Approximately 20.
- *Shape.*—Cylindric.
- *Apex.*—Obtuse.
- *Average length.*—Approximately 1 cm.
- *Average width.*—Approximately 0.2 cm.
- *Color.*—At first opening: Near 2A. At maturity: Near 7A. At fading: Near 17D.

Peduncle:
- *Length.*—At terminal end (shortest): Approximately 8 cm. At lateral end (longest): Approximately 11 cm.
- *Strength.*—Moderate.
- *Color.*—Near 137C.
- *Habit.*—Erect.
- *Surface texture.*—Lightly pubescent.

Inflorescence bud:
- *Length.*—Approximately 1 cm.
- *Diameter.*—Approximately 1 cm.
- *Form.*—Globular.
- *Color.*—Near 66D.

Phyllaries:
- *Appearance.*—Matte.
- *Texture.*—Lightly pubescent.
- *Number.*—Approximately 30 to 40.
- *Shape.*—Ovate.
- *Margin.*—Entire.
- *Apex.*—Acute.
- *Diameter.*—Approximately 0.3 cm.
- *Length.*—Approximately 0.5 cm.
- *Color.*—Upper side: Near 138A. Under side: Near 138A.

REPRODUCTIVE ORGANS

Ray florets:
- *Number of pistils per flower.*—1.
- *Stigma shape.*—2 branched.
- *Stigma color.*—Near 6A.
- *Style color.*—Near 6D.
- *Style length.*—Approximately 0.6 cm.
- *Stamens.*—Absent.

Disc florets:
- *Number of pistils per flower.*—1.
- *Stigma shape.*—Cylindric.

*Style length.*—Approximately 0.5 cm.
*Number of stamens per flower.*—Approximately 5.
*Anther shape.*—Tubular.
*Anther color.*—Near 6A.
*Pollen color.*—Near 7A.

OTHER CHARACTERISTICS

Seed production: Commercially, this plant is not used or observed in a stage wherein seeds would be produced. Therefore, seed production has not been observed to date.

Disease resistance: Neither resistance nor susceptibility to diseases and pests have been observed to date in this cultivar.

What is claimed is:

1. A new and distinct variety of Chrysanthemum plant named 'Gedi One Jam' as herein illustrated and described.

* * * * *